United States Patent [19]

Devlin

[11] Patent Number: 4,855,315
[45] Date of Patent: Aug. 8, 1989

[54] USE OF ZOFENOPRIL FOR THE TREATMENT OF RHEUMATOID ARTHRITIS

[75] Inventor: Richard G. Devlin, Sea Girt, N.J.

[73] Assignee: E. R. Squibb & Sons, Inc., Princeton, N.J.

[21] Appl. No.: 240,015

[22] Filed: Sep. 2, 1988

[51] Int. Cl.$^4$ ............................................. A61K 31/40
[52] U.S. Cl. ..................................... 514/422; 514/423
[58] Field of Search ................................ 514/422, 423

[56] References Cited

U.S. PATENT DOCUMENTS

| 4,235,885 | 11/1980 | Sundeen et al. | 424/177 |
|---|---|---|---|
| 4,263,293 | 4/1981 | Sundeen et al. | 424/248.5 |
| 4,297,275 | 10/1981 | Sundeen et al. | 260/112.5 |
| 4,316,906 | 2/1982 | Ondetti et al. | 424/274 |
| 4,327,111 | 4/1982 | Sundeen et al. | 424/278 |
| 4,382,081 | 5/1983 | Sundeen et al. | 424/177 |
| 4,424,354 | 1/1984 | Sundeen et al. | 544/299 |

OTHER PUBLICATIONS

Johnsen et al., "Immunosuppressive Action of Captopril Blocked by Prostaglandin Synthetase Inhibitor", Lancet, May 2, 1981, p. 1005.
Kallenberg et al., "Captopril and the Immune System", Lancet, Jul. 11, 1981, p. 92.
Merlet et al., "Captopril in Rheumatoid Arthritis", Revue Du Rheumatisme, XVth International Congress of Rheumatology, 1981, #1389 (Abstract).
Martin et al., "Captopril, A New Long Term Agent for Treating Rheumatoid Arthritis", The Heberden Society Annual Meeting and Oration (1982).
Martin et al., "Captopril: A New Treatment for Rheumatoid Arthritis", Lancet, Jun. 16, 1984, p. 1325.
Drury et al., "Captopril in Rheumatoid Arthritis", Lancet, Jul. 7, 1984, pp. 36 and 37.
Jaffe, "Angiotensin Converting Inhibitors in Rheumatoid Arthritis", Arthritis and Rheumatism, 27(7): 840 (1984).
Traficante et al., "Angiotensin Converting Enzyme Inhibitors and Rheumatoid Arthritis", Arthritis and Rheumatism, 28:480 (1985).
"Criteria for Diagnosis and Classification of Rheumatic Diseases", JAMA, 224(5): pp. 799 to 802 (1973).
Dixon et al., "Biochemical and Clinical Changes Occurring During the Treatment of Rheumatoid Arthritis with Novel Antirheumatoid Drugs", International Journal of Clinical Pharmacology in Research, V(1):25-33 (1985).
Jaffe, "Adverse Effects Profile of Sulfhydryl Compounds in Man", American Journal of Medicine, 80:471 (Mar., 1986).
"Angiotensin Converting Enzyme Inhibitors", Kostis et al. editors, Alan R. Liss, Inc., New York (1987), pp. 109 and 203.
Ward et al., "Interim Observations on the Benefits/Risk of Azathioprine Versus D-Penicillamine in the Treatment of Rheumatoid Arthritis", Ann. Rheum. Dis. 41 (Suppl): 23 (1982).
Williams et al., "Comparison of Low-Dose Oral Pulse Methotrexate and Placebo in the Treatment of Rheumatoid Arthritis", Arthritis and Rheumatism 28:721 (1985).
Pinals et al., "Preliminary Criteria for Clinical Remission in Rheumatoid Arthritis", Arthritis and Rheumatism 24:1308 (1981).

Primary Examiner—Stanley J. Friedman
Attorney, Agent, or Firm—Timothy J. Gaul; Donald J. Barrack

[57] ABSTRACT

Zofenopril, and pharmaceutically acceptable salts thereof, can be used for the treatment of rheumatoid arthritis.

2 Claims, No Drawings

USE OF ZOFENOPRIL FOR THE TREATMENT OF RHEUMATOID ARTHRITIS

BACKGROUND OF THE INVENTION

Rheumatoid arthritis is a lifelong, crippling, multisystem disease whose principal manifestation is joint inflammation. The prevalence of definite rheumatoid arthritis in the United States is approximately 1 percent (2,400,000 individuals). This estimated prevalence increases to 3 percent (7,200,000 individuals) when a more liberal definition of disease as specified by the American Rheumatism Association ("probable" and "possible" rheumatoid arthritis) is applied.

In the majority of individuals the disease is characterized by a fluctuating and variable course with lifelong periods of exacerbation and regression, but with ever worsening joint deformity and systemic disability. Approximately 10 percent of patients develop only a short-lived inflammatory process which remits spontaneously without permanent residua, while at the opposite end of the spectrum another 10 percent experience a relentlessly progressive disease leading rapidly to marked deformity and disability. The principal manifestation of rheumatoid arthritis is joint inflammation and deformity, usually accompanied by constitutional symptoms such as weakness, easy fatigability, anorexia or weight loss. Approximately 10–20 percent of individuals with definite rheumatoid arthritis experience significant extra-articular manifestation including vasculitis, skeletal muscle weakness and atrophy, polyneuropathy, pleuropulmonary disease, pericarditis or hematologic abnormalities.

Chemotherapeutic agents available for the treatment of rheumatoid arthritis are characterized by low efficacy and high toxicity. These agents fall into categories including steroids, nonsteroidal anti-inflammatory agents (NSAID's) and disease modifying anti-rheumatoid drugs (DMARD's). The NSAID's which include salicylates, as well as ibuprofen, fenoprofen, naproxen, piroxicam, tolmetin, indomethacin, sulindac, meclofenamate and others are primariy cycloxygenase inhibitors, inhibiting production of prostaglandins, prostacycline and thromboxanes. Thus, they all produce nonspecific analgesic, anti-inflammatory and antipyretic effects and are prescribed for the control of a variety of inflammatory states. Although they are perceived to be quite potent, in fact none have been demonstrated to be more effective than aspirin in the treatment of rheumatoid arthritis. NSAID's are generally prescribed as first line therapy for this condition and are administered episodically for control of acute exacerbation of disease. Patients commonly develop tachyphylaxis or therapeutic tolerance to these agents over time and it is common practice for individuals to be switched frequently from one to another agent in the group. It is unclear whether such decreased efficacy is a function of disease progression or physiologic tolerance. Despite their status as first line treatment for rheumatoid arthritis, the NSAID's are associated with a wide spectrum of toxic side effects, especially at the doses needed to control rheumatoid arthritis. All are associated with gastrointestinal irritation (and bleeding), azotemia, platelet dysfunction, liver function abnormalities, bone marrow depression and exacerbation of allergic conditions such as rhinitis or asthma. Although the incidence of each of these effects varies somewhat with the specific agent, elderly patients receiving diuretics, common in populations with rheumatoid arthritis, may be at higher than average risk for such phenomena.

The classification of drugs as DMARD's is somewhat of a misomer as none of these agents have been clearly shown to modify the progression of rheumatoid arthritis, although some rheumatologists believe that D-penicillamine or gold may delay the progression of radiologic abnormalities. In fact the Food and Drug Administration (FDA) appear to prefer the designation SAARD's (slow acting anti-rheumatic drugs) to more accurately identify the most unifying feature of these agents—the fact that clinical efficacy does not appear for weeks or months. Drugs in the category include D-penicillamine, gold salts (both parenteral and oral forms), hydroxychloroquine, azathioprine, methotrexae and cyclophosphamide, although the latter three agents are often classified as cytotoxic agents rather than DMARD's. Due to their considerable toxicity, these drugs are usually employed as second line therapy after patients become less responsive to NSAID's, but are usually given in conjunction with an NSAID. Generally these drugs are reserved for patients only with the most severe forms of rheumatoid arthritis and are rarely used early in the course of the disease. Over the course of their disease, patients are frequently switched from one agent to another due to intolerable toxicity or progressive lack of efficacy. Unlike the former group of compounds, agents in this category may produce improvement in such serologic markers of disease activity as titers of rheumatoid factor or sedimentation rate. However, formidable toxicity is associated with each and "black box" warnings are incorporated into the FDA approved labelling for drugs in this category. Gold salts are associated with a high incidence of rash, bone marrow toxicity (occasionally life threatening), proteinuria and severe diarrhea whereas hydroxychloroquine is associated with retinopathy, blood dyscrasias and a high incidence of dermatologic abnormalities including depigmentation and alopecia. Approximately 30% of patients receiving D-penicillamine develop significant proteinuria. Thrombocytopenia, rash or taste disturbances are also common. Azathioprine and cyclophosphamide are both associated with severe gastrointestinal and hematologic abnormalities as well as with an increased risk or neoplasia.

In view of this lack of effective, reasonably nontoxic chemotherapy for the treatment of rheumatoid arthritis, many new agents are in various phases of clinical development, including a variety of NSAID's and NSAID-prodrugs; gamma interferon, eicosapentaenoic acid, cyclosporin, interleuken-1 inhibitors, PAF antagonists and other immunomodulating agents are exemplary.

Dixon et al., "Biochemical and Clinical Changes Occurring During the Treatment of Rheumatoid Arthritis with Novel Antirheumatoid Drugs", *International Journal of Clinical Pharmacology in Research*, V(1):25–33 (1985) report that while it would be useful to discover more compounds with antirheumatoid activity, there are no adequate animal models of rheumatoid arthritis for the assessment of such compounds. A human screening system is reported by Dixon et al. and the testing of captopril in that system is also reported. Antirheumatoid activity is reported for captopril based on the results of that screening. Captopril is an angiotensin converting enzyme inhibitor having the chemical name 1-[(2S)-3- mercapto-2-methylpropionyl]-L-proline.

Jaffe, "Adverse Effects Profile of Sulfhydryl Compounds in Man", *American Journal of Medicine,* 80:471 (March, 1986) describes the use of sufhydryl containing compounds in the treatment of rheumatoid arthritis. The compounds described are penicillamine, 5-thiopyridoxine, pyrithioxine, α-mercaptopropionylglycine and captopril. In discussing these compounds, Jaffe states "Although these compounds show considerable variation in their chemical structure . . . , the sulfhydryl group is the fundamental requirement for antirheumatic activity in all of them." In discussing the need for more compounds in this class, Jaffe also states "Unfortunately, there is currently no means of predicting either efficacy or toxicity, short of an individual clinical trial".

(cis)-1-[D-3-(Benzoylthio)-2-methyl-1-oxopropyl]-4-(phenylthio)-L-proline (and its pharmaceutically acceptable salts) is an angiotensin converting enzyme inhibitor; see, for example, U.S. Pat. No. 4,316,906; issued February 23, 1982, which describes the compound and its salts. The approved nonproprietary name of the compound is zofenopril. Zofenopril is a prodrug of (cis)-1-(D-3-mercapto-2-methyl-1-oxopropyl)-4-(phenylthio)-L-proline.

BRIEF DESCRIPTION OF THE INVENTION

Zofenopril, and pharmaceutically acceptable salts thereof, can be used for the treatment of rheumatoid arthritis in a human host. The compound can be administered orally, topically (including transdermally) or parenterally (e.g., subcutaneously, intramuscularly, intravenously or intraperitoneally) in a suitable dosage form. Because rheumatoid arthritis is a chronic condition that is treated over an extended period of time, it is preferable that the compound be administered orally or topically.

The dose of zofenopril (or a pharmaceutically acceptable salt thereof) used to treat rheumatoid arthritis in a human host will, of course, vary with the severity of the disease and with the size of the patient. As will be seen from the Detailed Description of the Invention, an open unblinded study was run to ascertain the utility of zofenopril, calcium (i.e., the calcium salt of zofenopril) in the treatment of rheumatoid arthritis. In that study, patients received 30 mg per day of zofenopril, calcium for two weeks and 60 mg per day of zofenopril, calcium for the remainder of a twenty-four week period. It is believed that an effective dose of zofenopril or a pharmaceutically acceptable salt thereof is between 7.5 mg/day to 240 mg/day.

DETAILED DESCRIPTION OF THE INVENTION

The use of zofenopril, calcium in the treatment of rheumatoid arthritis was studied in an open unblinded study with no control population. Patients were selected who had established evaluable, rheumatoid arthritis. Therapy with NSAID's was optimized at least one month prior to enrollment and held constant throughout the study. Patients received 30 mg per day of zofenopril, calcium for two weeks and 60 mg per day of zofenopril, calcium for the remainder of a twenty-four week period. Clinical and laboratory parameters of rheumatoid arthritis were evaluated prior to and at one month intervals during therapy and at the end of a two month wash out period (after therapy had ended). The drug was administered using 30 mg zofenopril, calcium tablets. The following is an outline of the study:

A. General Considerations

This was an open study, utilizing 30 mg zofenopril, calcium tablets. The length of the treatment period for each individual patient was 6 months.

A patient could be discontinued from treatment at the discretion of the investigator due to intolerance, side effects, intercurrent illness or the request of the patient.

B. Patient Population

Patients had a primary diagnosis of active, definite or classical rheumatoid arthritis of adult onset and of greater than 6 months duration, meeting the diagnostic criteria of the American Rheumatism Association (ARA) (see AMA, 224(5):799 (1973). In addition to the ARA criteria, patient selection criteria for this study included:

1. Active disease, i.e., six or more swollen joints that were evaluable (possibly responsive to therapy) and at least two of the following: (a) nine or more evaluable joints, tender on pressure, (b) 45 minutes or more of morning stiffness, (c) Westergren erythrocyte sedimentation rate of 28 mm/hour or greater.

2. Inadequate control of disease with therapeutic doses of aspirin, low-dose steroids or NSAID's.

3. Constant (for at least 1 month prior to enrollment) optimal dose of aspirin, NSAID and/or steroids (maximum daily dose of prednisone was 10mg).

C. Drug Administration

Patients received a 30 mg zofenopril calcium tablet once a day for the first 2 weeks of the study and twice a day for the remaining 22 weeks of the study.

D. Patients' Visits and Evaluations

Patients visited the clinic for hematological evaluation and urinalysis biweekly for the first 3 months of the study and monthly thereafter. Patients visited the clinic monthly for clinical evaluation of rheumatic disease, laboratory evaluations for serum chemistry and certain serological tests. Examination of he status of rheumatoid activity included determination of the number of painful and tender joints, the number of swollen joints, duration of morning stiffness, grip strength, erythrocyte sedimentation rate, rheumatoid factor, C-reactive protein, the patient's opinion regarding the severity of his disease and the physician's opinion regarding the severity of the patient's disease. The same patient was examined by the same physician at approximately the same time of day, when possible, throughout the study.

E. Patient Withdrawal

Once the test medication was initiated, patients were to be withdrawn if any of the following laboratory abnormalities occurred:

a. The white blood cell count fell below $3000/mm^3$ or the absolute polymorphonuclear cell count fell below $1500/mm^3$.

b. The count fell below $100,000/mm./^3$.

c. Proteinuria exceeded 1.0g/24 hours.

If either a, b, or c occurred, the drug was to be discontinued and the results confirmed by a repeat test. If the repeated results failed to confirm the abnormality, therapy could be reinstituted. If the patient was withdrawn for any of the above, the patient was to be monitored as deemed necessary by the investigator until resolution occurred. In actual fact, none of the patients in this study was discontinued for abnormalities listed under a, b or c.

F. Patient Self-Assessment

1. The patient completed a questionnarie to assess general and specific activities including his ability (degree of difficulty) to handle personal needs including dressing and grooming, arising, eating, walking, hygiene, grip and various other activities.

2. The physician completed a questionnaire regarding the patient's morning stiffness and the onset of fatigue for the day preceding the visit.

3. The patient and the physician described the current state of arthritis disease activity on a scale of asymptomatic, mild, moderate, severe and very severe.

G. Physician's Assessment

1. Joint Count and Joint Evaluation

Two different assessments were done for each joint. The first assessment (referred to as joint count) included a determination of pain on motion (or tenderness on pressure where appropriate) and degree of swelling. The joint count for tenderness on pressure and/or pain on motion was assessed according to the following scale: 0=none, 1=positive response on questioning, 2=spontaneous response elicited, 3=withdrawal by patient on examination, 9=not applicable. Joint swelling was assessed as: 0=none, 1=detectable synovial thickening without loss of bony contours, 2=loss of distinctiveness of bony contours, 3=bulging synovial thickenin with cystic characteristics, 9=not applicable. The joint count was done at screening and at monthly intervals during the study. The joints to be evaluated (right and left) were fingers (DIP 2, DIP 3, DIP 4, DIP 5, PIP 2, PIP 3, PIP 4, PIP 5, MCP 1, MCP 2, MCP 3, MCP 4 and MCP 5), wrist, elbow, shoulder, acromio-clav, sterno-clav, temp.-mandib., toes (IP1, DIP & PIP 2, DIP & PIP 3, DIP & PIP 4, DIP & PIP 5, MTP 1, MTP 2, MTP 3, MTP 4 and MTP 5) mid-tarsal, ankle, knee and hip. The second assessment (referred to as joint evaluation) included a determination of joint involvement (joint with any physical findings characteristic for rheumatoid arthritis), joint activity (an active joint exhibits signs of inflammation such as pain, tenderness, swelling or effusions) and joint response potential (a joint with active disease which, in the opinion of the investigator, should respond to anti-arthritic medication).

The three assessments for joint evaluation were: 0=no, 1=yes and 9=not applicable. It should be noted that an "involved" joint may or may not be "active" and an "active" joint may or may not have "response potential." The joint evaluation was done only at screening.

2. Grip Strength

A mercury column sphygmomanometer with standard grip bag which registers a minimum of 250 mmHg was used. The system was inflated to 20 mmHg before measuring grip strength of the patient. The patient squeezed the cuff as hard as possible. The pressure at the level maintained by squeezing (not the initial bounce) was recorded. Three readings were recorded for each hand, alternating hands.

H. Criteria For Assessing Improvement

The following definitions were utilized to characterize what was considered important or meaningful improvement for several variables, including joint counts and scores and patient and physician assessment of disease severity:

1. Therapeutic remissions (6) - a minimum of 5 of the following for at least 2 consecutive, months: morning stiffness of <15 minutes, no fatigue, no joint pain by history, no joint tenderness, no joint swelling, and Westergren ESR of <20 mm/hour in men and <30 mm/hour in women.

2. Important improvement in joint swelling or joint pain/tenderness - improvement by 50% or more in the number of swollen (tender) joints, i.e., the patient showed swollen (tender) joint improvement if the number of joints improved exceeded the number of joints worsened by at least 50% of the joints initially involved and capable of response. Improvement was defined as change in swelling (tenderness) to none or improvement from severe to mild. Worsening was defined as involvement of a previously uninvolved joint or a change in swelling (tenderness) to severe in a joint that was previously involved to a moderate or mild degree. For example, a patient with 10 moderately swollen joints with 8 joints improved and 3 joints worsened during the trial would have significant joint improvement, but if 4 joints improved and 2 joints worsened, significant joint improvement would have not occurred.

3. Important improvement in patient assessment- Important improvement in patient assessment by at least 2 grades or to grade 1.

4. Important improvement in physician assessment - improvement in physician assessment by at least 2 grades or to grade 1.

I. Further Particulars of Methods For Evaluating Rheumatoid Arthritis That Were Given to Examining Physicians 1. Duration of Morning Stiffness Note the times at which patient usually rises. Ask if he is stiff. If so, ask by what time the stiffness wears off or when he "limbers up". Estimate the duration of his stiffness and write done to the nearest quarter hour. If the stiffness wears off slowly over a period of an hour or so, take the time of beginning of the change as the endpoint.

2. Grip Strength

The grip strength should be measured using a special rubber cuff. This cuff measures 7×4 cm, deflated, and approximately 15cm. in length and 15 cm. in circumference when inflated. The manometer and special cuff should be used only for the purposes of measuring grips, and the same manometer and cuff should be used for the duration of the entire trial. The mercury column should be clean and open. The filter should be clean and should be renewed frequently.

Inflate the system to 20 mmHg. Test the cuff once to assure that the mercury level returns to 20 mm level. Instruct the patient to hold the cuff in the right hand and squeeze as hard as possible. Make sure the long axis of the cuff is centered in the palm, and that the thumb is centered over the middle of the bag. Do not allow the patient to either pinch the end of the cuff, or rest his forearm on the table, or push the hand or cuff against the table, since all these maneuvers result in falsely high values. It is essential that maximum effort be made, and that the patient try his best. After each test of the right hand, test the left hand; then repeat the procedure until three tests on each hand are completed.

Record the readings in the appropriate spaces on the form. Record all three readings for both hands in sequence even if one of the readings seems at variance with the others. Do not subtract 20 from the recorded readings. If the patient is unable to grip the manometer, report a reading of 20, and make a note on the form.

In the event that a standard cuff is unavailable, fold a rubber-containing part of a blood pressure cuff until it forms a rectangle measuring approximately 14×7 cm. (about 6×3 inches). If possible, secure the cuff by stitching, and use the same cuff for duration of the study.

3. Joint Count (Spread, or Articular Index)

To estimate the total "amount" of active joint inflammation, all the peripheral joints are examined for tenderness on pressure, pain on passive motion, or swelling. (Pay no attention to fluid, heat, or restricted motion.) Elicit tenderness by squeezing the knuckles, by pressing directly with the thumbs on the carpal mosaics. Put the other joints through a full range of passive motion. To elicit jaw pain, ask the patient to bite firmly. PAIN is the end-point. Tick each 'positive' joint on chart, as 1, each negative joint as 0.

4. Erythrocyte Sedimentation Rate

The Westergren method must be used. The anticoagulant must be 3.8% sodium citrate. Exactly 2.0 ml of blood should be added to 0.5 ml of 3.8% sodium citrate in a tube, which is then inverted promptly for mixing. A blue topped Becton Dickinson (#3204xF37) vacutainer has 1ml of a 3.33 solution of sodium citrate and will draw approximately 4 ml of blood, and meets this requirement. Sedimentation should take place for exactly 1 hour in a vertical 200 mm-long sedimentation pipette having 2.5 mm inner diameter. Recording the result in millimeters of sedimentation per hour on the forms is self-explanatory.

J. Additional Explanation of Certain Parameters

1. C-Reactive Protein

C-reactive protein was assessed at the clinical laboratories of the participating physicians. It reflects in a general way the magnitude of the inflammatory process present in the patient.

2. Disease Index

Using a formula that took into account all of the parameters in the physician's assessment of the patient's disability, a disease index was calculated.

3. Joint Swelling Score

The joint swelling score was calculated using a formula that took into account the degree of swelling of each of the patient's joints as evaluated by the examining physician.

4. Joint Pain Score

The joint pain score was calculated using a formula that took into account the degree of pain of each of the patient's joints as evaluated by the examining physician.

5. Subjective Joint Pain Score

The subjective joint pain score was based on the patient's assessment of his joint pain expressed on a visual analog scale.

The following tables present a tabulation of the results of the above-described study.

When pre-dose and 6-month values were compared, improvements during treatment with zofenopril calcium were most evident in patients' reports of subjective pain, severity of joint pain, degree of joint swelling, duration of morning stiffness and number of swollen and painful joints. The disease index, which is a composite measure of many subjective evaluations, also showed a significant effect. Laboratory parameters that reflect the activity of the disease (e.g., C-reactive protein and rheumatoid factor levels) also indicated improvement.

When pre-dose and 4-month results were compared, all the parameters showed improvement.

Grip Strength Right Hand (mm of Hg)

| | Month of Study | | | | | | | |
|---|---|---|---|---|---|---|---|---|
| Subj | 0 | 1 | 2 | 3 | 4 | 5 | 6 | 8 |
| 1 | 36.7 | 31.3 | 32.7 | 35.3 | 32.7 | 38.7 | 44.0 | 34.0 |
| 2 | 113.3 | 139.3 | 134.0 | 112.7 | 150.7 | 175.3 | 153.3 | 140.0 |
| 3 | 75.3 | 66.0 | 73.3 | 93.3 | 109.3 | 108.0 | 92.7 | 80.7 |
| 4 | 68.7 | 97.3 | 80.0 | 92.0 | 110.0 | 108.0 | 112.7 | 127.3 |
| 5 | 68.0 | 42.7 | 35.3 | 47.3 | 48.0 | 39.3 | 45.3 | |
| 6 | 158.7 | 148.7 | 137.3 | 169.3 | 150.7 | 110.0 | 122.0 | 52.0 |
| 7 | 82.0 | 149.3 | 126.7 | 121.3 | 127.3 | 126.0 | 128.7 | 101.3 |
| 8 | 147.3 | 158.0 | 170.0 | 166.7 | 180.7 | 168.7 | 173.3 | 162.7 |
| 9 | 109.3 | 122.7 | 142.0 | 144.7 | 130.0 | 130.7 | 116.0 | |
| 10 | 76.0 | 66.7 | 71.3 | 52.7 | 73.3 | 62.0 | 64.7 | 35.3 |
| 11 | 110.0 | | 99.3 | 138.7 | 132.0 | 118.7 | 113.3 | |
| 12 | 30.7 | 38.7 | 38.7 | 38.0 | 38.7 | 32.0 | 37.3 | |
| 13 | 124.0 | 98.7 | 116.7 | 102.7 | 118.7 | 104.0 | 124.0 | 100.0 |
| 15 | 112.7 | 66.7 | 85.3 | 103.3 | 120.7 | 118.0 | 123.3 | 80.0 |
| 16 | 233.3 | 260.0 | 284.0 | 279.3 | 280.7 | 118.0 | 123.3 | 300.0 |
| 17 | 54.7 | 30.0 | 50.0 | 47.3 | 56.0 | 65.7 | 57.3 | 45.0 |
| 18 | 99.3 | 118.0 | 130.0 | 126.7 | 134.0 | 125.0 | 138.0 | 134.0 |
| 19 | 71.3 | 38.0 | 38.0 | 66.7 | 73.3 | 84.0 | 95.3 | 43.0 |
| 20 | 54.7 | 59.3 | 79.3 | 65.3 | 69.3 | 78.0 | 60.0 | |
| 21 | 156.0 | 165.3 | 180.7 | 125.3 | 147.3 | | | |
| 22 | 111.3 | 80.7 | 76.7 | 84.0 | 95.3 | 93.0 | 103.0 | 43.0 |
| Mean | 99.7 | 98.9 | 103.9 | 105.4 | 113.3 | 104.0 | 101.4 | 98.6 |
| SD | 46.3 | 57.6 | 59.0 | 55.5 | 54.8 | 41.2 | 37.4 | 67.6 |
| SE | 10.1 | 12.9 | 12.9 | 12.1 | 11.9 | 9.0 | 8.4 | 17.5 |
| LL | 89.6 | 86.0 | 91.0 | 93.2 | 101.3 | 95.0 | 93.0 | 81.1 |
| UL | 109.8 | 111.7 | 116.7 | 117.5 | 125.2 | 113.0 | 109.7 | 116.0 |

Grip Strength Left Hand (mm of Hg)

| | Month of Study | | | | | | | |
|---|---|---|---|---|---|---|---|---|
| Subj | 0 | 1 | 2 | 3 | 4 | 5 | 6 | 8 |
| 1 | 36.0 | 34.7 | 46.7 | 42.7 | 43.3 | 46.0 | 42.7 | 38.7 |
| 2 | 136.7 | 145.3 | 154.7 | 138.7 | 156.7 | 162.7 | 156.7 | 138.0 |
| 3 | 77.3 | 78.0 | 77.3 | 95.3 | 96.7 | 118.7 | 95.3 | 80.0 |
| 4 | 62.7 | 83.3 | 75.3 | 65.3 | 106.0 | 93.3 | 94.7 | 118.0 |
| 5 | 74.7 | 48.0 | 60.7 | 52.0 | 32.7 | 44.0 | 41.3 | |
| 6 | 153.3 | 119.3 | 137.3 | 183.3 | 139.3 | 142.0 | 128.7 | 61.3 |
| 7 | 92.7 | 120.7 | 114.0 | 100.7 | 117.3 | 120.0 | 109.3 | 86.0 |
| 8 | 106.0 | 114.0 | 132.0 | 136.0 | 156.0 | 145.3 | 125.3 | 130.7 |
| 9 | 103.3 | 95.3 | 122.7 | 127.2 | 120.0 | 91.3 | 78.0 | |
| 10 | 67.3 | 54.0 | 62.7 | 35.3 | 58.0 | 50.7 | 58.7 | 47.3 |
| 11 | 120.7 | | 86.7 | 136.0 | 112.7 | 106.7 | 107.3 | |
| 12 | 29.3 | 48.0 | 26.7 | 35.3 | 34.0 | 32.0 | 34.7 | |
| 13 | 107.3 | 93.0 | 114.0 | 100.0 | 120.0 | 109.3 | 120.7 | 90.0 |
| 15 | 124.7 | 65.3 | 68.0 | 96.7 | 114.0 | 104.7 | 90.0 | 74.0 |
| 16 | 210.0 | 234.0 | 250.0 | 269.3 | 256.0 | 104.7 | 90.0 | 285.0 |
| 17 | 58.7 | 56.0 | 61.3 | 82.7 | 74.7 | 76.7 | 60.0 | 45.0 |
| 18 | 95.3 | 114.7 | 112.7 | 116.0 | 136.0 | 120.0 | 119.0 | 145.0 |
| 19 | 60.0 | 41.3 | 38.0 | 57.3 | 66.0 | 81.3 | 68.7 | 53.0 |
| 20 | 51.3 | 41.3 | 64.0 | 60.7 | 68.0 | 71.0 | 63.0 | |
| 21 | 123.3 | 75.3 | 155.3 | 78.7 | 107.3 | | | |
| 22 | 94.0 | 88.7 | 84.0 | 78.0 | 90.0 | 93.0 | 106.0 | 53.0 |
| Mean | 94.5 | 87.5 | 97.3 | 99.4 | 105.0 | 98.5 | 89.5 | 96.3 |
| SD | 41.3 | 45.5 | 49.9 | 53.7 | 49.4 | 35.9 | 32.3 | 60.9 |
| SE | 9.0 | 10.2 | 10.9 | 11.7 | 10.8 | 7.8 | 7.2 | 15.7 |
| LL | 85.5 | 77.3 | 86.5 | 87.7 | 94.2 | 90.7 | 82.3 | 80.6 |
| UL | 103.5 | 97.7 | 108.2 | 111.1 | 115.9 | 106.3 | 96.7 | 112.1 |

Erythrocyte Sedimentation Rate (ml of sedimentation/hour)

| | Month of Study | | | | | | | |
|---|---|---|---|---|---|---|---|---|
| Subj | 0 | 1 | 2 | 3 | 4 | 5 | 6 | 8 |
| 1 | 54.90 | 12.40 | 15.10 | 7.70 | 16.60 | 30.40 | 45.15 | 57.70 |
| 2 | 35.80 | 28.40 | 19.40 | 23.60 | 5.10 | 11.70 | 9.00 | 17.90 |
| 3 | 10.60 | 10.10 | 3.90 | 2.00 | 0.10 | 0.10 | 16.30 | 28.50 |
| 4 | 15.20 | 24.80 | 18.80 | 12.50 | 27.20 | 16.90 | 22.20 | 11.80 |
| 5 | 4.80 | 15.60 | 10.30 | 10.40 | 21.20 | 15.90 | 22.20 | 12.7 |
| 6 | 15.20 | 24.80 | 18.80 | 12.50 | 27.20 | 16.90 | 22.20 | 11.80 |
| 7 | 100.00 | 24.60 | 34.90 | 11.00 | 24.30 | 24.00 | 28.30 | 44.10 |
| 8 | 9.60 | 5.40 | 12.60 | 9.80 | 4.10 | 23.00 | 31.50 | 46.40 |
| 9 | 43.30 | 34.50 | 32.00 | 16.60 | 21.70 | 31.10 | 39.00 | |
| 10 | 50.30 | 42.50 | 43.90 | 31.90 | 37.30 | 39.90 | 35.80 | 57.30 |
| 11 | | 93.70 | 67.50 | 43.80 | 55.50 | 39.80 | 31.40 | |
| 12 | 67.00 | 70.10 | 45.10 | 35.80 | 51.00 | 46.70 | 38.90 | |
| 13 | 5.60 | 5.90 | 5.50 | 23.90 | 0.80 | 2.50 | 4.20 | 23.90 |
| 15 | 10.90 | 4.60 | 8.50 | 3.50 | 5.10 | 3.80 | 16.60 | 15.80 |
| 16 | 18.10 | 8.80 | 3.90 | 0.50 | 5.50 | 4.10 | 4.20 | 0.2 |
| 17 | 31.90 | 47.50 | 24.90 | 22.90 | 25.00 | 20.50 | 16.30 | 38.4 |
| 18 | 37.20 | 31.70 | 26.40 | 25.00 | 18.10 | 16.00 | 19.20 | 13.50 |
| 19 | 38.00 | 23.40 | 30.70 | 27.10 | 10.20 | 11.10 | 6.50 | 12.20 |

-continued

| | | | | | | | | |
|---|---|---|---|---|---|---|---|---|
| 20 | 10.90 | 5.50 | 3.10 | 5.20 | 0.10 | 0.10 | 0.10 | |
| 21 | 18.10 | 30.40 | 15.80 | 32.80 | 24.10 | 36.70 | | |
| 22 | 68.80 | 57.60 | 76.20 | 62.00 | 30.20 | 26.80 | 50.00 | 12.20 |
| Mean | 32.31 | 28.68 | 24.63 | 20.02 | 19.54 | 19.90 | 22.95 | 25.28 |
| SD | 25.00 | 22.68 | 19.58 | 15.03 | 15.38 | 13.62 | 13.98 | 17.39 |
| SE | 5.74 | 5.07 | 4.38 | 3.36 | 3.44 | 3.05 | 3.21 | 4.49 |
| LL | 26.57 | 23.61 | 20.26 | 16.66 | 16.10 | 16.86 | 19.74 | 20.79 |
| UL | 38.05 | 33.75 | 29.01 | 23.39 | 22.98 | 22.95 | 26.16 | 29.76 |

C—Reactive Protein

| | Month of Study | | | | | | | |
|---|---|---|---|---|---|---|---|---|
| Subj | 0 | 1 | 2 | 3 | 4 | 5 | 6 | 8 |
| 1 | 48.00 | 52.00 | 9.00 | 12.00 | 16.00 | 20.00 | 48.00 | 10.00 |
| 2 | 60.00 | 52.00 | 40.00 | 50.00 | 36.00 | 38.00 | 40.00 | 12.00 |
| 3 | 14.00 | 20.00 | 8.00 | 3.00 | 10.00 | 6.00 | 16.00 | 10.00 |
| 4 | 25.00 | 50.00 | 25.00 | 75.00 | 16.00 | 16.00 | 68.00 | 60.00 |
| 5 | 20.00 | 10.00 | 10.00 | 22.00 | 37.00 | 15.00 | 23.00 | 19 |
| 6 | 25.00 | 50.00 | 25.00 | 75.00 | 16.00 | 16.00 | 68.00 | 60.00 |
| 7 | 55.00 | 47.00 | 42.00 | 3.00 | 9.00 | 28.00 | 35.00 | 36.00 |
| 8 | 32.00 | 30.00 | 32.00 | 30.00 | 30.00 | 54.00 | 71.00 | 70.00 |
| 9 | 10.00 | 75.00 | 53.00 | 38.00 | 3.00 | 56.00 | 40.00 | |
| 10 | 12.00 | 9.00 | 20.00 | 23.00 | 23.00 | 8.00 | 12.00 | 22.00 |
| 11 | 55.00 | 75.00 | 40.00 | 29.00 | 58.00 | 35.00 | 44.00 | |
| 12 | 76.00 | 76.00 | 70.00 | 96.00 | 104.00 | 86.00 | 92.00 | |
| 13 | 20.00 | 20.00 | 13.00 | 30.00 | 20.00 | 40.00 | 20.00 | 30.00 |
| 15 | 12.00 | 14.00 | 8.00 | 6.00 | 7.00 | 6.00 | 2.00 | 5.00 |
| 16 | 53.00 | 20.00 | 39.00 | 23.00 | 35.00 | 23.00 | 29.00 | 30 |
| 17 | 24.00 | 40.00 | 38.00 | 32.00 | 30.00 | 26.00 | 27.00 | 36 |
| 18 | 40.00 | 12.00 | 7.00 | 12.00 | 15.00 | 5.00 | 6.00 | 5.00 |
| 19 | 32.00 | 22.00 | 30.00 | 18.00 | 15.00 | 13.00 | 8.00 | 20.00 |
| 20 | 22.00 | 34.00 | 14.00 | 7.00 | 8.00 | 13.00 | 9.00 | |
| 21 | 31.00 | 15.00 | 7.00 | 15.00 | 11.00 | 3.00 | | |
| 22 | 58.00 | 38.00 | 75.00 | 31.00 | 23.00 | 41.00 | 52.00 | 20.00 |
| Mean | 34.48 | 36.24 | 28.81 | 30.00 | 24.86 | 26.10 | 35.50 | 27.81 |
| SD | 18.57 | 21.38 | 19.74 | 24.51 | 21.82 | 20.39 | 24.50 | 19.61 |
| SE | 4.15 | 4.78 | 4.41 | 5.48 | 4.88 | 4.56 | 5.62 | 5.06 |
| LL | 30.32 | 31.46 | 24.40 | 24.52 | 19.98 | 21.54 | 29.88 | 22.75 |
| UL | 38.63 | 41.02 | 33.22 | 35.48 | 29.74 | 30.65 | 41.12 | 32.88 |

Morning Stiffness

| | Month of Study | | | | | | | |
|---|---|---|---|---|---|---|---|---|
| Subj | 0 | 1 | 2 | 3 | 4 | 5 | 6 | 8 |
| 1 | 375 | 150 | 350 | 345 | 285 | 285 | 300 | 270 |
| 2 | 165 | 15 | 90 | 0 | 90 | 30 | 75 | 60 |
| 3 | 90 | 90 | 60 | 30 | 30 | 30 | 30 | 150 |
| 4 | 120 | 0 | 210 | 120 | 60 | 90 | 30 | 60 |
| 5 | 150 | 210 | 180 | 210 | 240 | 280 | 210 | |
| 6 | 90 | 180 | 180 | 60 | 150 | 135 | 150 | 540 |
| 7 | 20 | 30 | 30 | 30 | 0 | 15 | 10 | 75 |
| 8 | 60 | 120 | 120 | 150 | 120 | 60 | 120 | 180 |
| 9 | 210 | 210 | 120 | 0 | 0 | 0 | 195 | |
| 10 | 75 | 30 | 150 | 30 | 5 | 10 | 10 | 30 |
| 11 | 285 | 270 | 330 | 300 | 210 | 150 | 340 | |
| 12 | 270 | 390 | 120 | 330 | 390 | 150 | 180 | |
| 13 | 960 | 60 | 30 | 60 | 90 | 65 | 30 | 30 |
| 15 | 60 | 45 | 60 | 30 | 20 | 30 | 20 | 570 |
| 16 | 0 | 0 | 60 | 0 | 0 | 0 | 0 | 0 |
| 17 | 120 | 315 | 60 | 0 | 1200 | 120 | 120 | 150 |
| 18 | 135 | 150 | 150 | 180 | 150 | 180 | 160 | 270 |
| 19 | 150 | 180 | 0 | 0 | 0 | 0 | 0 | 0 |
| 20 | 120 | 240 | 180 | 120 | 180 | 60 | 75 | |
| 21 | 60 | 0 | 0 | 930 | 0 | 270 | | |
| 22 | 390 | 170 | 420 | 180 | 210 | 0 | 15 | 0 |
| Mean | 186 | 136 | 138 | 148 | 163 | 93 | 104 | 159 |
| SD | 202 | 109 | 112 | 206 | 256 | 93 | 99 | 178 |
| Se | 44 | 24 | 24 | 45 | 56 | 20 | 22 | 46 |
| LL | 142 | 112 | 114 | 103 | 108 | 73 | 81 | 113 |
| UL | 230 | 160 | 162 | 193 | 219 | 114 | 126 | 205 |

Joint Count (number of painful joints)

| | Month of Study | | | | | | | |
|---|---|---|---|---|---|---|---|---|
| Subj | 0 | 1 | 2 | 3 | 4 | 5 | 6 | 8 |
| 1 | 26 | 19 | 17 | 16 | 12 | 13 | 7 | 8 |
| 2 | 27 | 16 | 10 | 9 | 5 | 4 | 5 | 11 |
| 3 | 15 | 25 | 19 | 20 | 16 | 21 | 26 | 28 |
| 4 | 26 | 15 | 8 | 15 | 7 | 8 | 13 | 6 |
| 5 | 39 | 32 | 45 | 39 | 45 | 41 | 42 | |
| 6 | 8 | 2 | 7 | 9 | 20 | 10 | 14 | 24 |
| 7 | 25 | 5 | 6 | 6 | 3 | 5 | 5 | 6 |
| 8 | 19 | 30 | 38 | 27 | 25 | 19 | 24 | 25 |
| 9 | 26 | 14 | 12 | 15 | 3 | 13 | 18 | |
| 10 | 28 | 32 | 24 | 33 | 32 | 34 | 35 | 42 |
| 11 | 44 | 44 | 36 | 34 | 31 | 33 | 35 | |
| 12 | 25 | 18 | 16 | 37 | 41 | 32 | 27 | |
| 13 | 22 | 28 | 19 | 17 | 26 | 17 | 18 | 30 |
| 15 | 12 | 16 | 14 | 10 | 8 | 9 | 9 | 10 |
| 16 | 33 | 17 | 6 | 4 | 3 | 3 | 0 | 1 |
| 17 | 42 | 30 | 20 | 6 | 9 | 20 | 7 | 28 |
| 18 | 7 | 9 | 11 | 12 | 9 | 10 | 13 | 12 |
| 19 | 27 | 21 | 22 | 24 | 14 | 8 | 12 | 16 |
| 20 | 18 | 23 | 22 | 23 | 16 | 11 | 8 | |
| 21 | 5 | 12 | 5 | 8 | 3 | 11 | | |
| 22 | 28 | 30 | 22 | 23 | 23 | 17 | 18 | 16 |
| Mean | 24 | 21 | 18 | 18 | 17 | 16 | 17 | 18 |
| SD | 10 | 10 | 11 | 11 | 12 | 10 | 11 | 11 |
| SE | 2 | 2 | 2 | 2 | 3 | 2 | 2 | 3 |
| LL | 22 | 19 | 16 | 16 | 14 | 14 | 14 | 15 |
| UL | 26 | 23 | 20 | 21 | 19 | 18 | 19 | 20 |

Joint Swelling (number of swollen joints)

| | Month of Study | | | | | | | |
|---|---|---|---|---|---|---|---|---|
| Subj | 0 | 1 | 2 | 3 | 4 | 5 | 6 | 8 |
| 1 | 29 | 13 | 15 | 7 | 10 | 6 | 10 | 12 |
| 2 | 35 | 26 | 17 | 18 | 10 | 10 | 14 | 18 |
| 3 | 29 | 30 | 37 | 36 | 28 | 27 | 36 | 42 |
| 4 | 24 | 23 | 18 | 11 | 17 | 14 | 16 | 7 |
| 5 | 28 | 20 | 31 | 24 | 29 | 31 | 27 | |
| 6 | 19 | 19 | 20 | 10 | 18 | 14 | 21 | 21 |
| 7 | 23 | 19 | 13 | 9 | 9 | 10 | 10 | 12 |
| 8 | 36 | 31 | 36 | 25 | 25 | 24 | 26 | 29 |
| 9 | 32 | 29 | 29 | 29 | 20 | 33 | 25 | |
| 10 | 35 | 29 | 28 | 29 | 31 | 32 | 33 | 34 |
| 11 | 24 | 33 | 20 | 11 | 13 | 24 | 17 | |
| 12 | 31 | 18 | 18 | 20 | 22 | 21 | 20 | |
| 13 | 17 | 23 | 17 | 18 | 20 | 16 | 10 | 26 |
| 15 | 19 | 19 | 16 | 12 | 10 | 12 | 13 | 15 |
| 16 | 26 | 14 | 4 | 7 | 5 | 2 | 0 | 1 |
| 17 | 42 | 28 | 28 | 18 | 25 | 20 | 20 | 33 |
| 18 | 17 | 12 | 16 | 19 | 15 | 20 | 15 | 13 |
| 19 | 35 | 28 | 32 | 18 | 17 | 15 | 4 | 9 |
| 20 | 14 | 18 | 19 | 17 | 15 | 11 | 13 | |
| 21 | 20 | 20 | 8 | 10 | 6 | 11 | | |
| 22 | 20 | 20 | 10 | 10 | 3 | 8 | 11 | 9 |
| Mean | 26 | 22 | 21 | 17 | 17 | 17 | 17 | 19 |
| SD | 7 | 6 | 9 | 8 | 8 | 9 | 9 | 11 |
| SE | 2 | 1 | 2 | 2 | 2 | 2 | 2 | 3 |
| LL | 25 | 21 | 19 | 15 | 15 | 15 | 15 | 16 |
| UL | 28 | 24 | 23 | 19 | 18 | 19 | 19 | 22 |

Joint Swelling Score (total of scores for each joint)

| | Month of Study | | | | | | | |
|---|---|---|---|---|---|---|---|---|
| Subj | 0 | 1 | 2 | 3 | 4 | 5 | 6 | 8 |
| 1 | 40 | 19 | 19 | 8 | 14 | 11 | 15 | 20 |
| 2 | 49 | 31 | 18 | 19 | 11 | 10 | 14 | 20 |
| 3 | 38 | 44 | 52 | 54 | 38 | 38 | 46 | 60 |
| 4 | 35 | 31 | 20 | 12 | 20 | 14 | 17 | 9 |
| 5 | 56 | 28 | 44 | 33 | 40 | 47 | 32 | |
| 6 | 27 | 24 | 23 | 15 | 22 | 18 | 24 | 34 |
| 7 | 27 | 23 | 16 | 9 | 9 | 11 | 10 | 15 |
| 8 | 70 | 52 | 63 | 47 | 40 | 41 | 53 | 47 |
| 9 | 48 | 38 | 33 | 35 | 24 | 42 | 29 | |
| 10 | 55 | 34 | 41 | 37 | 52 | 46 | 43 | 53 |
| 11 | 40 | 51 | 30 | 16 | 19 | 31 | 20 | |
| 12 | 40 | 21 | 21 | 25 | 25 | 24 | 21 | |
| 13 | 19 | 27 | 21 | 22 | 23 | 17 | 10 | 30 |
| 15 | 23 | 27 | 22 | 16 | 14 | 17 | 16 | 22 |
| 16 | 35 | 14 | 5 | 7 | 5 | 2 | 0 | 1 |
| 17 | 71 | 34 | 35 | 23 | 29 | 24 | 24 | 43 |
| 18 | 20 | 14 | 18 | 24 | 14 | 22 | 18 | 14 |
| 19 | 59 | 39 | 42 | 20 | 21 | 18 | 4 | 10 |
| 20 | 14 | 20 | 22 | 18 | 18 | 12 | 13 | |
| 21 | 25 | 27 | 11 | 11 | 6 | 36 | | |
| 22 | 25 | 28 | 11 | 12 | 3 | 64 | 68 | 10 |
| Mean | 39 | 30 | 27 | 22 | 21 | 26 | 24 | 26 |
| SD | 16 | 10 | 14 | 12 | 12 | 15 | 17 | 17 |
| SE | 4 | 2 | 3 | 3 | 3 | 3 | 4 | 4 |
| LL | 35 | 28 | 24 | 19 | 19 | 23 | 20 | 21 |
| UL | 42 | 32 | 30 | 25 | 24 | 29 | 28 | 30 |

Joint Pain Score (total of scores for each joint)

| | Month of Study | | | | | | | |
|---|---|---|---|---|---|---|---|---|
| Subj | 0 | 1 | 2 | 3 | 4 | 5 | 6 | 8 |

-continued

| | | | | | | | | |
|---|---|---|---|---|---|---|---|---|
| 1 | 31 | 22 | 25 | 17 | 21 | 16 | 12 | 13 |
| 2 | 46 | 23 | 12 | 10 | 5 | 6 | 6 | 13 |
| 3 | 19 | 35 | 27 | 30 | 18 | 27 | 31 | 33 |
| 4 | 46 | 21 | 8 | 16 | 9 | 9 | 14 | 8 |
| 5 | 85 | 44 | 68 | 58 | 72 | 65 | 59 | |
| 6 | 10 | 2 | 7 | 14 | 22 | 12 | 14 | 36 |
| 7 | 33 | 6 | 8 | 7 | 5 | 7 | 6 | 10 |
| 8 | 20 | 30 | 38 | 27 | 25 | 20 | 25 | 25 |
| 9 | 36 | 19 | 14 | 19 | 6 | 16 | 24 | |
| 10 | 39 | 48 | 32 | 43 | 55 | 45 | 40 | 73 |
| 11 | 74 | 86 | 50 | 45 | 38 | 45 | 50 | |
| 12 | 29 | 20 | 19 | 38 | 54 | 40 | 33 | |
| 13 | 25 | 33 | 24 | 23 | 33 | 25 | 24 | 37 |
| 15 | 14 | 22 | 20 | 10 | 8 | 11 | 9 | 12 |
| 16 | 47 | 19 | 6 | 4 | 4 | 3 | 0 | 1 |
| 17 | 71 | 42 | 24 | 7 | 11 | 22 | 9 | 39 |
| 18 | 9 | 11 | 12 | 14 | 9 | 10 | 13 | 13 |
| 19 | 40 | 27 | 26 | 25 | 16 | 8 | 12 | 17 |
| 20 | 23 | 27 | 26 | 23 | 18 | 11 | 8 | |
| 21 | 7 | 19 | 5 | 9 | 4 | 36 | | |
| 22 | 41 | 53 | 27 | 30 | 26 | 76 | 76 | 17 |
| Mean | 35 | 29 | 23 | 22 | 22 | 24 | 23 | 23 |
| SD | 21 | 18 | 15 | 14 | 19 | 20 | 19 | 18 |
| SE | 5 | 4 | 3 | 3 | 4 | 4 | 4 | 5 |
| LL | 31 | 25 | 19 | 19 | 18 | 20 | 19 | 19 |
| UL | 40 | 33 | 26 | 25 | 26 | 29 | 28 | 28 |

Disease Index

| | Month of Study | | | | | | | |
|---|---|---|---|---|---|---|---|---|
| Subj | 0 | 1 | 2 | 3 | 4 | 5 | 6 | 8 |
| 1 | 2.13 | 2.38 | 2.38 | 2.38 | 2.38 | 2.38 | 2.50 | 2.25 |
| 2 | 1.63 | 1.50 | 1.00 | 0.38 | 0.25 | 0.25 | 0.00 | 0.75 |
| 3 | 1.13 | 1.63 | 1.13 | 1.13 | 1.25 | 0.75 | 1.13 | 1.38 |
| 4 | 2.50 | 1.50 | 1.38 | 1.25 | 1.25 | 1.00 | 0.63 | 0.75 |
| 5 | 2.38 | 2.63 | 2.63 | 2.50 | 2.63 | 2.63 | 2.63 | |
| 6 | 0.13 | 0.38 | 0.00 | 0.00 | 0.13 | 0.00 | 0.25 | 1.88 |
| 7 | 1.75 | 1.25 | 1.25 | 0.75 | 0.63 | 0.50 | 0.50 | 0.50 |
| 8 | 0.50 | 0.88 | 1.25 | 0.13 | 0.38 | 0.38 | 0.50 | 0.50 |
| 9 | 2.13 | 1.63 | 1.13 | 1.13 | 1.00 | 0.88 | 1.38 | |
| 10 | 2.25 | 2.38 | 2.25 | 2.00 | 2.00 | 2.25 | 1.88 | 2.13 |
| 11 | 2.00 | 2.00 | 2.00 | 1.88 | 2.00 | 1.75 | 2.00 | |
| 12 | 2.88 | 3.00 | 3.00 | 3.00 | 3.00 | 3.00 | 3.00 | |
| 13 | 1.00 | 0.88 | 1.13 | 1.50 | 0.88 | 0.88 | 1.00 | 0.88 |
| 15 | 0.88 | 0.50 | 1.13 | 0.75 | 0.75 | 0.75 | 0.75 | |
| 16 | 0.25 | 0.00 | 0.00 | 0.00 | 0.00 | 0.00 | 0.00 | |
| 17 | 1.25 | 1.63 | 1.25 | 0.75 | 0.38 | 1.25 | 0.38 | |
| 18 | 1.38 | 1.13 | 1.13 | 1.13 | 1.00 | | | |
| 19 | 1.25 | 2.25 | 1.75 | 0.88 | 0.50 | 0.13 | 0.25 | |
| 20 | 1.25 | 1.25 | 1.13 | 1.00 | 0.75 | | | |
| 21 | 1.00 | 0.75 | 0.88 | 0.88 | 0.38 | | | |
| 22 | 2.25 | 2.13 | 2.38 | 2.13 | 2.13 | | | |
| Mean | 1.52 | 1.51 | 1.44 | 1.22 | 1.13 | 1.10 | 1.10 | 1.22 |
| SD | 0.74 | 0.77 | 0.76 | 0.81 | 0.86 | 0.93 | 0.94 | 0.66 |
| SE | 0.16 | 0.17 | 0.17 | 0.18 | 0.19 | 0.23 | 0.23 | 0.22 |
| LL | 1.36 | 1.34 | 1.27 | 1.04 | 0.94 | 0.88 | 0.88 | 1.00 |
| UL | 1.68 | 1.68 | 1.60 | 1.39 | 1.32 | 1.33 | 1.33 | 1.45 |

Joint Pain Score (Subjective; based on 0 to 1 assessment by patient)

| | Month of Study | | | | | | | |
|---|---|---|---|---|---|---|---|---|
| Subj | 0 | 1 | 2 | 3 | 4 | 5 | 6 | 8 |
| 1 | 0.64 | 0.73 | 0.49 | 0.61 | 0.61 | 0.81 | 0.97 | 0.84 |
| 2 | 0.55 | 0.46 | 0.31 | 0.10 | 0.00 | 0.21 | 0.19 | 0.69 |
| 3 | 0.67 | 0.66 | 0.26 | 0.39 | 0.12 | 0.50 | 0.77 | 0.70 |
| 4 | 0.52 | 0.59 | 0.31 | 0.21 | 0.72 | 0.63 | 0.15 | 0.18 |
| 5 | 0.84 | 0.68 | 0.80 | 0.48 | 0.71 | 0.53 | 0.52 | |
| 6 | 0.38 | 0.26 | 0.26 | 0.19 | 0.28 | 0.23 | 0.25 | 0.80 |
| 7 | 0.34 | 0.22 | 0.21 | 0.50 | 0.01 | 0.14 | 0.02 | 0.05 |
| 8 | 0.54 | 0.39 | 0.31 | 0.10 | 0.18 | 0.19 | 0.18 | 0.17 |
| 9 | 0.67 | 0.31 | 0.17 | 0.16 | 0.12 | 0.07 | 0.50 | |
| 10 | 0.53 | 0.79 | 0.68 | 0.69 | 0.69 | 0.66 | 0.71 | 0.91 |
| 11 | 0.71 | 0.74 | 0.61 | 0.62 | 0.72 | 0.67 | 0.46 | |
| 12 | 0.82 | 0.87 | 0.82 | 0.70 | 0.96 | 0.74 | 0.98 | |
| 13 | 0.30 | 0.32 | 0.41 | 0.66 | 0.64 | 0.55 | 0.64 | 0.55 |
| 15 | 0.39 | 0.72 | 0.43 | 0.33 | 0.27 | 0.36 | 0.62 | 0.84 |
| 16 | 0.25 | 0.33 | 0.15 | 0.01 | 0.00 | 0.36 | 0.62 | |
| 17 | 0.70 | 0.76 | 0.74 | 0.44 | 0.36 | 0.41 | 0.17 | 0.77 |
| 18 | 0.79 | 0.66 | 0.77 | 0.52 | 0.47 | 0.57 | 0.62 | 0.65 |
| 19 | 0.91 | 0.75 | 0.28 | 0.35 | 0.09 | 0.08 | 0.05 | |
| 20 | 0.74 | 0.84 | 0.71 | 0.44 | 0.45 | 0.23 | 0.11 | |
| 21 | 0.31 | 0.59 | 0.17 | 0.75 | 0.11 | 0.25 | | |
| 22 | 0.74 | 0.54 | 0.62 | 0.45 | 0.44 | 0.15 | 0.16 | 0.43 |
| Mean | 0.59 | 0.58 | 0.45 | 0.41 | 0.38 | 0.40 | 0.43 | 0.55 |
| SD | 0.19 | 0.20 | 0.23 | 0.21 | 0.28 | 0.22 | 0.29 | 0.29 |
| SE | 0.04 | 0.04 | 0.05 | 0.05 | 0.06 | 0.05 | 0.07 | 0.08 |
| LL | 0.55 | 0.54 | 0.40 | 0.37 | 0.32 | 0.35 | 0.37 | 0.47 |
| UL | 0.63 | 0.62 | 0.50 | 0.46 | 0.44 | 0.45 | 0.50 | 0.63 |

SD = standard deviation; SE = standard error;
LL = lower limit; UL = upper limit

What is claimed is:

1. A method of treating rheumatoid arthritis in a person in need thereof, which comprises administering to said person an effective amount of zofenopril or a pharmaceutically acceptable salt thereof.

2. A method of treating rheumatoid arthritis in accordance with claim 1 wherein zofenopril or a pharmaceutically acceptable salt thereof is administered orally.

* * * * *